US005843656A

United States Patent [19]
Bridgham et al.

[11] Patent Number: 5,843,656
[45] Date of Patent: Dec. 1, 1998

[54] RECOMBINANT CLONE SELECTION SYSTEM

[75] Inventors: John A. Bridgham, Hillsborough; John Brandis, Hercules; John Leong, San Francisco; Paul D. Hoeprich, Jr., Danville, all of Calif.

[73] Assignee: The Perkin-Elmer Corporation, Foster City, Calif.

[21] Appl. No.: 511,846

[22] Filed: Aug. 7, 1995

[51] Int. Cl.$^6$ .............................. C12Q 1/68; C12P 21/00; C12N 15/63; C07H 21/04
[52] U.S. Cl. ........................... 435/6; 435/69.1; 435/91.4; 435/252.3; 435/320.1; 536/23.1
[58] Field of Search .................. 435/69.1, 91.4, 435/172.3, 240.2, 252.3, 320.1, 6; 514/44; 536/23.1

[56] References Cited

U.S. PATENT DOCUMENTS 5,239,062  8/1993  Blattler et al. ........................... 530/396

FOREIGN PATENT DOCUMENTS

| | | | |
|---|---|---|---|
| 0 198 474 | 4/1986 | European Pat. Off. ........ | C12N 15/00 |
| WO 89/04203 | 11/1988 | WIPO ............................ | B01D 15/08 |
| WO 91/19567 | 6/1991 | WIPO ............................ | B01L 3/00 |
| WO 92/14819 | 2/1992 | WIPO ............................ | C12N 15/00 |
| WO 93/02360 | 7/1992 | WIPO ............................ | G01N 33/536 |
| WO 94/00581 | 6/1993 | WIPO ............................ | C12N 15/74 |
| WO 95/17509 | 12/1994 | WIPO ............................ | C12N 15/12 |
| WO 96/32486 | 4/1995 | WIPO ............................ | C12N 15/74 |
| WO 96/36696 | 5/1996 | WIPO ............................ | C12N 5/00 |
| WO 96/40943 | 6/1996 | WIPO ............................ | C12N 15/62 |

OTHER PUBLICATIONS

Jenkinson and Easingwood. Insertional inactivation of the gene encoding a 76–kilodalton cell surface polypeptide in *Streptococcus gordonii* challis has a pleiotropic effect on cell surface composition and properties. Infection and Immunity. vol. 58(11), Nov. 30, 1990.

Guilfoyle and Smith. A direct selection strategy for shotgun cloning and sequencing in the bacteriophage M13. Nucleic Acids Res.. vol. 22(1):100–107, Jan. 30, 1994.
Bernard et. al.. Positive–selection vectors using the F plasmid ccdB killer gene. Gene. vol. 148(1), Oct. 21, 1994.
Bernard et al. Gene 148: 71–74 (1994) Positive–selection vectors using the F plasmid ccdB killer gene.
Austin et al. Biotechniques 18(3):380–384 (1995) Visual Detection Method for Identifying Recombinant Bacterial Colonies.
Shabarova et al. Nucleic Acids Research 19 (15):4247–4251 (1991) Chemical ligation of DNA: The first non–enzymatic assembly of a biologically active gene.
Herrlein et al. Nucleic Acids Research 22 (23):5076–5078 (1994) Selective chemical autoligation on a double–stranded DNA template.
Peterson et al. Cell 54: 65–72 (1988) Genetic analysis of Monoclonal Antibody and HIV Binding Sites on the Human Lymphocyte Antigen CD4.

(List continued on next page.)

*Primary Examiner*—Nancy Degen
*Assistant Examiner*—William Sandals
*Attorney, Agent, or Firm*—Paul D. Grossman; Scott R. Bortner

[57] ABSTRACT

Cloning systems useful for the isolation of recombinant nucleic acid are disclosed in which the recombination of cloning-system nucleic acid and foreign nucleic acid is linked to the expression of a moiety on the surface of a host organism, the moiety being a first member of a binding pair. When recombination occurs between the nucleic acid and the foreign nucleic acid, the moiety is expressed on the surface of the host organism. The isolation of recombinant nucleic acid is then performed by attaching a second member of the binding pair to a solid support and contacting the host organism with the support. When the first member of the binding pair is expressed on the surface of the host organism, the host organism binds to the second member of the binding pair attached to the solid support, thereby selectively isolating those organisms.

10 Claims, 4 Drawing Sheets

OTHER PUBLICATIONS

Devlin et al. Science 249: 404–406 (1990) Random Peptide Libraries: A source of Specific Protein Binding Molecules.

Houghten et al. Nature 354: 84–86 (1991) Generation and use of synthetic peptide combinatorial libraries for basic research and drug discovery.

Wysocki et al. Proc. Natl. Acad. Sci. USA 75(6):2844–2848 (1978) "Panning" for lymphocytes: A method for cell selection.

Zheng et al BioTechniques 18(5):740–741 (1995) Immunological screening of homologous recombination in genes that encode surface antigens.

Scott et al Science 249:386–390 (1990) Searching for Peptide Ligands with an Epitope Library.

Lutz et al. Proc. Natl. Acad. Sci. USA 84:4379–4383 (1987) Syrinx 2A: AN improved λ phage vector designed for screening DNA libraries by recombination in vivo.

Stengelin et al. EMBO Journal 7(4): 1053–1059 (1988) Isolation of cDNAs for two distinct human Fc receptors by ligand affinity cloning.

Uber et al. BioTechniques 11(5):642–648 (1991) Application of Robotics and Image Processing to Automated Colony Picking and Arraying.

Jones et al. Nucleic Acids Research 20 (17): 4599–4606 (1992) Integration of image analysis and robotics into a fully automated colony picking and plate handling system.

Aruffo et al Proc. Natl. Acad. Sci. USA 84: 8573–8577 (1987) Molecular cloning of a CD28 cDNA by a high-efficiency COS cell expression system.

Huse et al Science 246: 1275–1281 (1989) Generation of a Large Combinatorial Library of the Immunoglobin repertoire in Phage Lambda.

Messing et al Proc. Natl. Acad. Sci. USA 74(9): 3642–3646 (1977) Filamentous coliphage M13 as a cloning vehicle: Insertion of a HindII fragment of the lac regulatory region in M13 replicative form in vitro.

Messing Methods in Enzymology 101: 20–78 (1983) New M13 Vectors for Cloning.

Aruffo et al EMBO Journal 6(11):3313–3316 (1987) Molecular cloning of two CD7 (T–cell leukemia antigen) cDNAs by a COS cell expression system.

Seed et al Proc. Natl. Acad. Sci. USA 84: 3365–3369 (1987) Molecular cloning of the CD2 antigen, the T–cell erythrocyte receptor, by a rapid immunoselection procedure.

Hochuli Genetic Engineering 12: 87–98 (1990) Purification of Recombinant Proteins with Metal Chelate Adsorbent.

Singhvi et al Science 264: 696–698 (1994) Engineering Cell Shape and Function.

Edlind et al. Plasmid expression vector using the lambda late promoter. Plasmid vol. 15:242–244, May 1, 1986.

Meyenberg et al. Promoters of the atp operon coding fro teh membrane–bound ATP synthase of *Escherichia coli* mapped by Tn10 insertion mutations. Mol. Gen. Genet. vol. 188:240–248, Dec. 2, 1988.

Solenberg et al. Method for selection of transposable DNA and characterization of a new insertion sequence, IS493, from *Streptom;yces lividans*. J. Bact. vol. 171(9):4807–4813, Sep. 1989.

Shen et al. Dominant negative reinoic acid receptor beta. Mech. Dev. vol. 40:177–189, Apr. 22, 1993.

Chou et al. Mapping of herpes virus–1 neurovirulence to gamma1–34.5, a gene nonessential for growth in culture. Science vol. 250:1262–1266, Nov. 30, 1990.

Ward et al. Vectors for $Cu^{++}$–inducible production of glutathioine S–transferase–fusioin proteins for single–step purification from yeast. Yeast. vol. 10:441–449, May 18, 1994.

RECOMBINANT CLONE SELECTION SYSTEM

BACKGROUND

This invention relates to the identification and selection of genetically transformed cells. More specifically, this invention describes a vector-host cloning system in which genetic transformation with foreign nucleic acid is accompanied by a measurable change in surface binding properties of a host organism.

The ability to selectively recombine genetic material from different organisms in vitro and to cause the resulting "recombinant" material to be replicated and/or used to direct the expression of proteins in a host organism, has transformed the study of biology and greatly enhanced its practical utility, e.g., Cohen et al., U.S. Pat. No. 4,237,224. Applications of this "cloning" or "recombinant nucleic acid" technology include the expression of medically useful human proteins in bacterial cell culture, the creation of immortalized genetic "libraries" containing the entire genome of a particular organism, and the segregation and replication of foreign nucleic acid in preparation for nucleic acid sequencing.

Generally, the cloning process includes the following steps: (i) foreign nucleic acid fragments are prepared having the appropriate size and cohesive end regions, the foreign nucleic acid being either a digest of genomic nucleic acid or cDNA; (ii) a vector nucleic acid is cleaved with one or more restriction enzymes, preferably at a unique site, to form a vector nucleic acid having cohesive end regions suitable for binding to the cohesive end regions of the foreign nucleic acid fragments, where the vector nucleic acid includes (a) elements which allow the inserted foreign nucleic acid fragments to survive and autonomously replicate in a host organism and (b) a selectable marker in order to facilitate the recognition and isolation of cells carrying the foreign nucleic acid; (iii) the foreign nucleic acid fragments are contacted with the cleaved vector nucleic acid under conditions favoring combination of the foreign nucleic acid fragments and the vector nucleic acid, and the vector and foreign nucleic acid are ligated together, thereby forming a recombinant vector-foreign nucleic acid; (iv) the recombinant vector-foreign nucleic acid is introduced into the host organism, thereby genetically transforming the host organism; (v) the host organisms containing the recombinant vector-foreign nucleic acid are separated from untransformed cells and cells containing only parent vector nucleic acid, and optionally, (vi) the separated cells are subjected to a secondary screen for specific nucleic acid inserts, e.g., by contacting with nucleic acid probes or by contacting their expressed proteins with antibody probes.

A key step in the above cloning process is the identification and isolation of host organisms which have been successfully transformed with recombinant vector-foreign nucleic acid, i.e., step (v) above. A number of products can result from the reaction of the cleaved vector nucleic acid with the foreign nucleic acid fragments. The products of the recombination reaction are a heterogeneous mixture of recombinant vector-foreign nucleic acid molecules together with religated parental vector molecules. In fact, for many systems, the vast majority of cells are transformed with parental vector nucleic acid only, e.g., less than 0.1% of the host organisms are transformed with vector-foreign nucleic acid. This low frequency of vector-foreign nucleic acid transformation creates a large background of cells containing no foreign nucleic acid, thereby dramatically increasing the effort required to perform any secondary screening. The automation of step (v) is a particularly important issue for large-scale cloning projects where millions of potential clones must be screened, e.g., the construction of libraries for genomic sequencing projects.

There are four methods that are commonly used to identify host organisms that contain recombinant vector-foreign nucleic acid, including (i) restriction analysis of small-scale preparations of plasmid nucleic acid, (ii) α-complementation, (iii) insertional inactivation, and, (iv) screening by hybridization (see Molecular Cloning 2nd Ed., Sambrook et al, Chapter 1, Cold Spring Harbor Laboratory Press (1989)).

In the restriction analysis method, a number of independently transformed host organisms are picked from a parent culture and grown up in small-scale cultures. Plasmid nucleic acids are isolated from each culture and then analyzed by digestion with restriction enzymes followed by gel electrophoresis.

In the α-complementation method, the cloning vectors carry a short segment of *Escherichia coli* nucleic acid that contains the regulatory sequences and the coding information for the first 146 amino acids of the β-galactosidase gene (lacZ). Embedded in this coding region is a polycloning site. These vectors are used in combination with host organisms that code for the carboxy-terminal portion of β-galactosidase. While neither the host-encoded nor the vector-encoded fragments are themselves active, they can associate to form an enzymatically active protein. This type of complementation is called α-complementation. The Lac+ bacteria that result from α-complementation are easily recognized because they form blue colonies in the presence of the chromogenic substrate X-gal. However, insertion of a fragment of foreign nucleic acid into the polycloning site of the vector results in the production of an amino-terminal fragment that is not capable of α-complementation. Host organisms carrying recombinant vectors therefore form white colonies. The recombinant vectors can then be visually identified and manually "picked" from the culture.

The insertional inactivation method is used with vectors that carry two or more antibiotic resistance genes and an appropriate distribution of restriction enzyme cleavage sites. The foreign nucleic acid and the vector nucleic acid are digested with restriction enzymes that recognize sites located in only a first antibiotic resistance gene. After ligating the two nucleic acids, the ligation mixture is used to transform *E. coli*. Transformants are selected that are resistant to the second antibiotic. Some of the colonies that grow in the presence of the second antibiotic will contain recombinant vectors; others will contain parental vector nucleic acid that has religated during ligation without insertion of foreign nucleic acid. To discriminate between the two types of transformants, separate plates containing the first or second antibiotic are inoculated with a number of colonies in patches in identical locations. The colonies that grow in the presence of the first antibiotic contain plasmids with active resistance genes, and it is unlikely that such plasmids contain insertions of foreign nucleic acid. It is likely that the colonies that do not grow in the presence of the first antibiotic but do grow in the presence of the second antibiotic carry the foreign nucleic acid sequences.

In hybridization screening techniques, a replica of the host organism colonies is transferred to a filter support, the cells are lysed releasing their nucleic acid, and the nucleic acid is then probed with labeled sequence-specific nucleic acid probes. The location of probe-positive colonies is then used to identify the location of recombinant cells on the original culture plate.

The above methods for identifying cells which have been transformed with recombinant vectors each require a number of cumbersome steps resulting in significant barriers to intelligent automation. Even the most streamlined α-complementation method requires the analyst to (i) grow-up the putatively transformed cells in a culture plate, (ii) visually identify cells having a specified color, (iii) pick cells having a specified color, and (iv) transfer the picked cells to a secondary location. While automated systems for picking individual colonies have been demonstrated, they require complicated robotic and image processing apparatus, making them unsuitable for cost effective, routine application, e.g., Uber et al., Biotechniques 11: 642–648 (1991); Jones et al., Nucleic Acids Research 20: 4599–4606 (1992). Moreover, because the α-complementation approach requires cells to be plated out, it is not amenable to the selection of cells which can not be grown on culture plates, e.g., certain eukaryotic tissue cells.

SUMMARY

The present invention is directed toward our discovery of a cloning system which facilitates the isolation of recombinant nucleic acid. Our system links the recombination event to the expression of a moiety at the surface of a host organism such that when recombination occurs, the moiety is expressed on the surface of the host, and in the absence of recombination, the moiety is not expressed on the surface of the host. Moreover, this differentially-expressed moiety is a member of a binding pair, the other member of which is attached to a solid support. Thus, when the moiety is expressed on the surface of the host organism, the host organism can be captured by binding to the solid support. The invention includes methods, apparatus, and compositions for using the cloning system.

An object of our invention is to provide a cloning system which is well suited for practical, low-cost automation of the recombinant selection process.

A further object of our invention is to provide a cloning system which does not traditionally require growing host organisms on a culture plate to identify and isolate cells which have been transformed with recombinant nucleic acid.

An additional object of our invention is to provide a cloning system which does not require visual identification of host organisms which have been transformed with recombinant nucleic acid.

Another object of our invention is to provide a cloning system which does not require mechanically picking selected cells from a culture plate.

Yet another object of our invention is to provide a cloning system which results in the placement of recombinant-transformed organisms at discrete, pre-defined locations on a solid support, each location containing only a single recombinant organism.

The foregoing and other objects of our invention are achieved by, in a first aspect referred to herein as the trans cloning system, a cloning system comprising a first nucleic acid, e.g., a host nucleic acid, and a second nucleic acid, e.g., a vector nucleic acid. The first nucleic acid includes a surface-expressed-moiety gene which codes for a surface-expressed moiety which is a member of a binding pair. The first nucleic acid further includes a first promoter sequence for promoting the expression of the surface-expressed-moiety gene and an operator which is functionally linked to the expression of the surface-expressed-moiety gene such that when a complementary repressor is bound to the operator, expression of the surface-expressed-moiety gene is repressed. The second nucleic acid includes a repressor gene and a second promoter sequence for promoting the expression of the repressor gene. The second nucleic acid further includes an insertion site located within the repressor gene such that when a foreign nucleic acid is inserted at the insertion site, expression of the repressor gene is insertionally inactivated.

One embodiment of the present invention includes a method for cloning and isolating recombinant nucleic acids using the above-described trans cloning system. In this method, the second nucleic acid is cleaved at the insertion site forming a cleaved second nucleic acid, then the cleaved second nucleic acid is contacted with a foreign nucleic acid under conditions sufficient to incorporate the foreign nucleic acid into the cleaved second nucleic acid, thereby forming a recombinant nucleic acid. The recombinant nucleic acid is then inserted into a host organism containing the first nucleic acid, and the host organism is grown-up for a time sufficient to express the surface expressed moiety (SEM) gene. Finally, the host organism is contacted with a solid support having attached thereto a moiety capable of specifically binding to the surface expressed moiety.

In a second aspect referred to herein as the cis cloning system, the present invention provides a nucleic acid capable of expression in a host organism useful for the isolation of recombinant nucleic acid which includes a surface-expressed-moiety gene along with a promoter sequence for promoting the expression of the surface-expressed-moiety gene. The nucleic acid of the invention further includes a first insertion site located downstream from the promoter sequence and upstream from the surface-expressed-moiety gene and a second insertion site located between the first insertion site and the surface-expressed-moiety gene. Finally, the nucleic acid of the invention includes an expression blocking sequence, located between the first insertion site and the second insertion site, which serves to block the expression of nucleic acid sequence located downstream from the expression blocking sequence, e.g., the SEM gene.

In one preferred embodiment, the present invention provides a method for cloning and isolating recombinant nucleic acid using the above described nucleic acid. In the method, the nucleic acid is cleaved at the first insertion site and at the second insertion site thereby forming a cleaved nucleic acid. Next, the cleaved nucleic acid is mixed with a foreign nucleic acid under conditions sufficient to incorporate the foreign nucleic acid into the cleaved nucleic acid, thereby forming a recombinant nucleic acid. The recombinant nucleic acid is then inserted into a host organism and the host organism is grown up for a time sufficient to express the surface expressed moiety gene. Finally, the host organism is contacted with a solid support having attached thereto a moiety capable of specifically binding to the surface expressed moiety.

In yet another aspect referred to herein as the tag cloning system, the present invention provides a cloning system useful for the isolation of recombinant nucleic acid which includes a tag moiety sequence which is adapted for lining to a foreign nucleic acid thereby forming an insertion sequence. In addition to the tag moiety sequence, the system includes a nucleic acid having a surface-protein gene coding for a protein which is expressed on the surface of a host organism. The nucleic acid further includes a promoter sequence for promoting the expression of the surface-protein gene and an insertion site located within the surface protein gene such that when the insertion sequence is inserted at the insertion site, the tag moiety sequence is expressed at the surface of the host organism.

One embodiment of the present invention includes a method for cloning and isolating recombinant nucleic acid using the above-described tag cloning system. In this method, the nucleic acid of the invention is cleaved at the insertion site thereby forming a cleaved nucleic acid. The tag moiety sequence is then linked to a foreign nucleic acid forming an insertion sequence. Next, the insertion sequence is contacted with the cleaved nucleic acid under conditions sufficient to incorporate the insertion sequence into the cleaved nucleic acid, thereby forming a recombinant nucleic acid. The recombinant nucleic acid is then inserted into a host organism and the host organism is grown up for a time sufficient to express the tag moiety sequence. Finally, the host organism is contacted with a solid support having attached thereto a moiety capable of specifically binding to the tag moiety.

In yet another aspect, referred to herein as the lethal gene inactivation system, the present invention provides a nucleic acid capable of expression in a host organism useful for the isolation of recombinant nucleic acid. The nucleic acid of the invention includes a surface-expressed-moiety gene along with a first promoter sequence for promoting the expression of the surface-expressed-moiety gene. The nucleic acid of the invention further includes a lethal gene whose expressed protein is lethal to the host organism and a second promoter sequence for promoting the expression of the lethal gene. Finally, the nucleic acid includes an insertion site located within the lethal gene such that when foreign nucleic is inserted at the insertion site the lethal gene is insertionally inactivated.

In one preferred embodiment, the invention includes a method for cloning and isolating recombinant nucleic acid using the lethal gene inactivation system. In this method, the nucleic acid of the invention is cleaved at the insertion site. The cleaved nucleic acid is then contacted with a foreign nucleic acid under conditions sufficient to incorporate the foreign nucleic acid into the cleaved nucleic acid, thereby forming a recombinant nucleic acid. The recombinant nucleic acid is then inserted into a host organism and the host organism is grown up for a time sufficient to express the lethal gene and the SEM gene. Finally, the host organism is contacted with a solid support having attached thereto a moiety capable of specifically binding to the SEM.

In yet another aspect, the present invention provides a host organism capture system. The system includes a solid support having a plurality of binding moieties attached thereto. The binding moieties are members of binding pairs, the complementary member of the binding pairs being differentially expressed on the surface of a host organism using any one of the above-described cloning systems. Preferably the binding moieties are located in a plurality of discrete anchor sites, each anchor site having dimensions such that only a single host organism can bind to a single anchor site.

These and other objects, features, and advantages of the present invention will become better understood with reference to the following description, drawings, and appended claims.

DESCRIPTION OF PREFERRED EMBODIMENTS

Generally, the present invention is directed toward our discovery of cloning systems useful for the isolation of recombinant nucleic acid. These systems link the recombination of vector nucleic acid and foreign nucleic acid to the expression of a moiety which is located at the surface of a host organism, the moiety being a first member of a binding pair. When recombination occurs between vector nucleic acid and foreign nucleic acid, the moiety is expressed on the surface of the host organism. Alternatively, when no recombination occurs, the moiety is not expressed on the surface of the host organism. The isolation of the recombinant nucleic acid is then performed by attaching a second member of the binding pair to a solid support and contacting the host organism with the support. When the first member of the binding pair is expressed on the surface of the host organism, the host organism binds to the second member of the binding pair attached to the solid support, thereby selectively removing those organisms from the host-organism suspension. In this way host organisms containing recombinant nucleic acid can be physically isolated from host organisms which lack such nucleic acid.

1. Trans Cloning System

In a first aspect of the present invention, hereinafter referred to as the "trans cloning system", the recombination of vector nucleic acid and foreign nucleic acid is linked to the expression of a surface-expressed moiety through the disruption of a repressor gene. When recombination has occurred, the repressor gene is insertionally inactivated, thereby allowing the expression of a SEM gene which is functionally linked to an operator which binds the repressor. Therefore, in the absence of recombination, a functional repressor is expressed, leading to the repression of the SEM gene. As used herein, "repressed" means that the level of expression is reduced by at least a factor of three relative to the level of expression observed in the absence of repression.

Figure 1A:
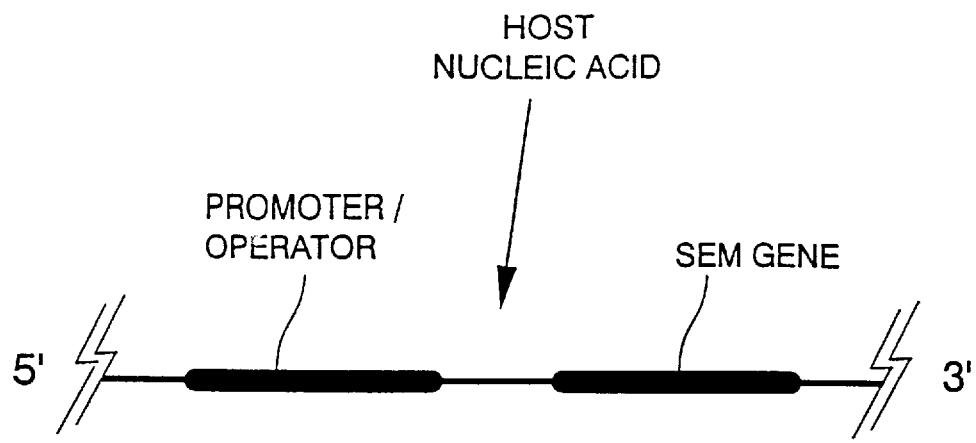
FIG. 1 shows a schematic diagram of the trans cloning system of the present invention.
Figure 1B:
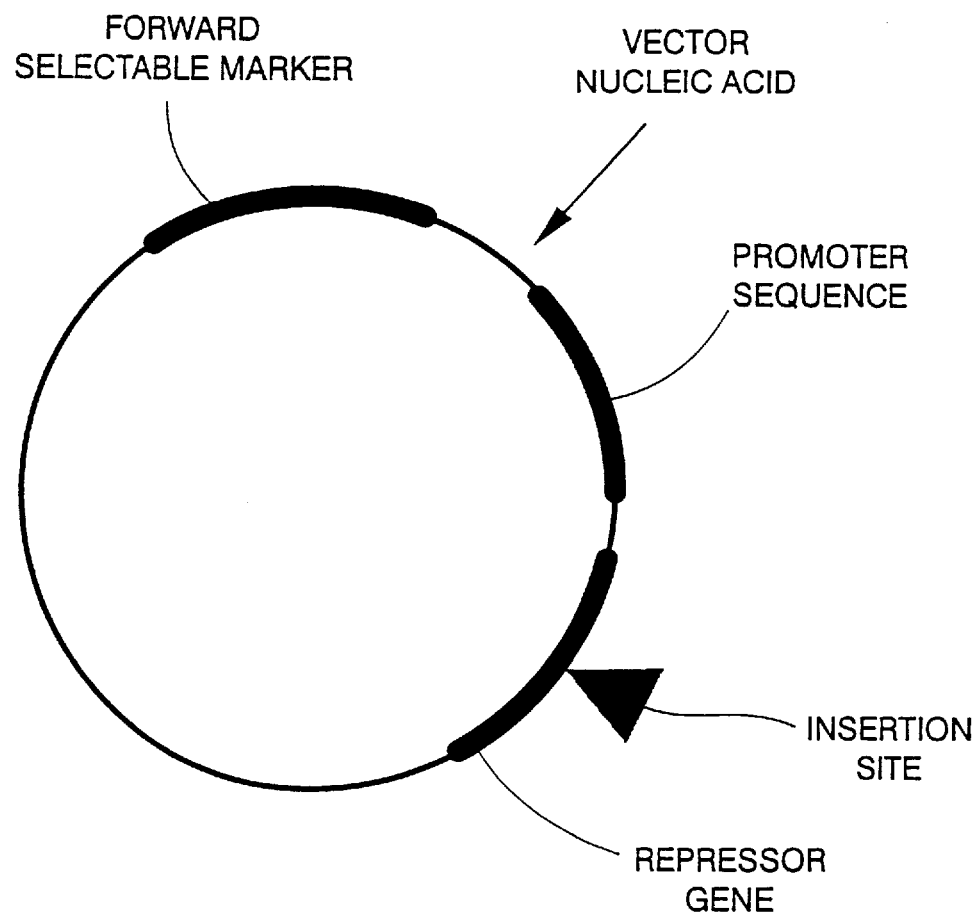

As indicated in FIG. 1, the trans cloning system is made up of two genetic elements: (i) a vector nucleic acid and (H) a host nucleic acid, the host nucleic acid being located within a host organism. In the preferred embodiment shown in FIG. 1, the host nucleic acid includes (i) a SEM gene, and (ii) a promoter/operator, wherein the promoter/operator is functionally linked to the SEM gene such that when a repressor is bound to the operator, expression of the SEM gene is repressed. The vector nucleic acid shown in FIG. 1 includes (i) a promoter sequence; (ii) a repressor gene, the repressor gene being functionally linked to the promoter sequence; and (iii) an insertion site, the insertion site being located within the repressor gene such that when a foreign nucleic acid is inserted at the insertion site, the repressor gene is insertionally inactivated. As used herein, the term "insertion site" refers to a location on a double or single stranded nucleic acid at which the nucleic acid may be cleaved in a sequence-specific manner, using a restriction endonuclease or any other like sequence-specific cleaving means, such that properly treated foreign nucleic acid may be ligated therein, e.g., a restriction site. As used herein, the term "ligate" refers to the joining of two strands of nucleic acid by either enzymatic means, e.g., using T4 nucleic acid ligase, *E. coli* nucleic acid ligase, or other like nucleic acid ligases, e.g., Current Protocols in Molecular Biology, Ausubel et al. eds., Current Protocols (1993), or using chemical means, e.g., Herrlein et al., Nucleic Acids Research, 22: 5076–78 (1994), and Shabarova et al., Nucleic Acids Research, 19: 4247–51 (1991).

In the present invention, the purpose of the vector nucleic acid is to (i) provide a means for the transport of foreign nucleic acid into a host organism, (ii) provide for the maintenance and/or replication of the foreign nucleic acid in the host organism, and (iii) provide part of the linkage between genetic recombination and the expression of the SEM molecule at the surface of the host organism. Preferred vectors may be based on plasmids, cosmids, viruses, or retroviruses, e.g., M13mp, bacteriophage λ, cos 202, cos 203, bovine papilloma virus, Epstein-Barr virus, or any other like vectors, e.g., Molecular Cloning Second Edition, Sambrook et al., eds., Cold Spring Harbor Laboratory Press (1989). The vector nucleic acid may be either linear or circular in form. However, preferably the vector nucleic acid is circular.

As used herein, the term "repressor" refers to molecules which act to inhibit the expression of a target structural gene by binding to a specific operator functionally linked to the target structural gene, and the term "repressor gene" refers to a gene which codes for the repressor molecule. The term "operator" as used herein refers to a specific site on a nucleic acid at which a repressor specifically binds, such specific binding blocking the expression of an associated structural gene. Typically, repressors act by preventing the transcription of a structural gene into mRNA by blocking the attachment of RNA polymerase to the nucleic acid. Therefore, when repressor molecules are not present, RNA polymerase can bind to nucleic acid and initiate transcription, and, when repressor molecules are present, the RNA polymerase is prevented from binding to the nucleic acid, and transcription, and therefore expression, is effectively blocked.

The repressor gene may be either constitutively expressed or inducibly expressed. Preferably, the repressor gene is constitutively expressed. More preferably, the repressor gene is overexpressed, where, as used herein, the term "overexpressed" refers to a level of expression which is greater than normal physiological levels. Such constitutive overexpression provides tight control of the expression of the structural gene with which the repressor molecule is associated.

Preferred repressor-operator systems include the lac operon, the gal operon, the alpha2-ste6 system, the cI repressor of the $\lambda_{PL}$ promoter, or any other like repressor-operator system, e.g., Maximizing Gene Expression, Reznikoff et al., Butterworths (1986).

In an important feature of the present invention, an insertion site is located within the repressor gene, where, as used herein, the term "insertion site" refers to a location on a nucleic acid at which the nucleic acid can be cleaved at a sequence-specific location using a sequence-specific cleaving agent, e.g., a restriction enzyme, or chemical cleaving agents, e.g., Dervan, Nature 359: 87–88, and foreign nucleic acid can be inserted. The location of the insertion site within the repressor gene is such that when a foreign nucleic acid is inserted at the site, the expression of the repressor gene is effectively inactivated, i.e., the repressor gene is insertionally inactivated. Typically, an insertion site is a nucleic acid sequence at which one or more restriction enzymes specifically cut the nucleic acid, the ends of the cuts being such that properly treated foreign nucleic acid can be ligated into the insertion site. Preferably, the insertion site may be cut by a plurality of different restriction enzymes or other sequence-specific cutting agents, thereby providing greater flexibility as to the types of foreign nucleic acids which can be accommodated. Numerous such restriction enzymes are available from commercial sources, each enzyme recognizing a different nucleic acid sequence, e.g., Stratagene Cloning Systems, La Jolla Calif., 1994 Catalog. Preferably, the restriction site defining the insertion site occurs only once in the vector nucleic acid so that the insertion site is uniquely defined in the vector, e.g., cleaving agents which recognize sequences of at least six bases in length.

In one preferred embodiment of the present invention, the vector nuceic acid includes a promoter sequence for promoting the expression or overexpression of the repressor gene. The promoter may be either constitutive, e.g., tet promoter, bla promoter, or any other like constitutive promoter, or regulatory, e.g., lac, $\lambda_{PL}$, Tac, or any other like regulatory promoter. The promoter is located so as to be functionally linked to the expression of the repressor gene. Preferably, the promoter is regulatory.

Preferably, the vector nucleic acid of the present invention further includes a forward selectable marker for selecting between transformed and untransformed host organisms. Preferred forward selectable markers include genes conferring antibiotic resistance. Thus, when a population of host organisms is challenged with a selection agent, e.g., an antibiotic, only those organisms which have been transformed with the vector nucleic acid will survive. Exemplary forward selectable markers include the $amp^R$ gene.

The host organism may be eucaryotic, viral, bacterial, or plant. The host organism must be (i) capable of being transformed with the vector nucleic acid and (i) provide a suitable environment for the maintenance and/or replication of the vector nucleic acid and the host nucleic acid. Exemplary host organisms include COS cells, CHO cells, *E. coli* or any other suitable host organism. Preferably, the host organism is a bacteria, e.g., *E. coli*.

As indicated in FIG. 1, the host nucleic acid of the present invention includes two elements: (i) a SEM gene coding for a surface-expressed moiety and (ii) an operator for binding the repressor coded for by the repressor gene located on the vector nucleic acid.

The SEM gene codes for a moiety that is expressed by the host, then transported to the surface of the host such that it is presented to the exterior surface of the host organism. Moreover, the SEM is a member of a binding pair, where, as used herein, the term "binding pair" refers to a pair of molecular entities, e.g., binding moieties, which specifically and strongly bind to one another under suitable conditions, one member of the binding pair being differentially expressed on the surface of a host organism, and the other member of the binding pair being attached to a solid support. Exemplary binding pairs include ligand/receptor pairs, antigen/antibody pairs, the biotin/avidin pair, and the like. A more thorough discussion of the properties of preferred SEM molecules and preferred binding pairs will be presented in a following section.

The operator located on the host nucleic acid serves to regulate the expression of the SEM gene. Moreover, the operator is functionally linked to the expression of the SEM gene such that when the repressor is bound to the operator, expression of the SEM gene is repressed. Preferably the operator is located upstream from the SEM gene. As used herein the term "upstream" refers to a direction towards the 5' end of a sense strand of a double-stranded nucleic acid, and the term "downstream" refers to a direction towards the 3' end of a sense strand of a double-stranded nucleic acid. Preferred operator/repressor pairs have been discussed above.

It will be clear to one of ordinary skill in the molecular biology art that the present invention could be carried out by inverting the location of the various elements of the trans cloning system. That is, the invention could just as well be carried out by placing the SEM gene and its associated operator on the vector nucleic acid and placing the repressor gene and its associated promoter on the host nucleic acid. In another permutation, all elements could be located on the vector nucleic acid.

Methods utilizing the trans cloning system utilize cloning techniques well known in the art of molecular biology. First, the vector nucleic acid is cleaved at the insertion site using an appropriate restriction endonuclease under conditions sufficient to render the restriction enzyme active. The cleaved vector nucleic acid is contacted with a foreign nucleic acid under conditions sufficient to incorporate the foreign nucleic acid into the vector nucleic acid at the insertion site, e.g., by enzymatic ligation, thereby forming a recombinant vector nucleic acid. The recombinant vector nucleic acid is then inserted into the host organism by either transfection, transformation, or conjugation, the particular mode of insertion being dependent on the nature of the recombinant vector nucleic acid and the host organism. The host organism is then grown up to provide an opportunity for the expression of the surface-expressed moiety. Finally, the host organism is contacted with a solid support which has been functionalized with a moiety capable of specifically binding to the SEM (see below). If a particular host organism contains a recombinant vector nucleic acid, the host organism will express the SEM at its outer surface and will therefore bind to the functionalized solid support.

2. Cis Cloning System

In a second aspect of the present invention, hereinafter referred to as the "cis cloning system", the recombination of vector nucleic acid and foreign nucleic acid is linked to the expression of a SEM by linking the recombination event with the removal of a segment of vector nucleic acid which blocks the expression of the SEM gene.

Figure 2:
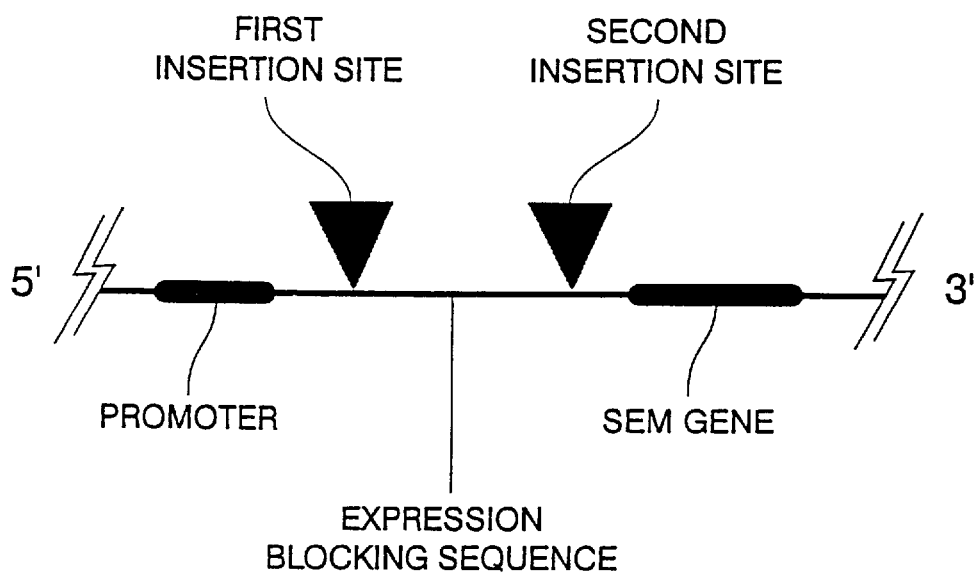
FIG. 2 shows a schematic diagram of the of cis cloning system of the present invention.

As shown in FIG. 2, the preferred vector nucleic acid of the cis cloning system includes five elements: (i) a promoter sequence, (ii) a first insertion site, (iii) a second insertion site, (iv) an expression blocking sequence, and (v) a SEM gene. Preferably, the vector is a circular nucleic acid.

The purpose of the promoter sequence is to promote the expression of downstream nucleic acid sequence, particularly the SEM gene. Preferred promoter sequences have been previously described herein.

Preferably, the first and second insertion sites are chosen such that different restriction enzymes cleave each site, and that each restriction site occurs only once in the vector nucleic acid. By making each of the two restriction sites different from the other, the opportunity for religation of the parent vector after restriction without incorporation of the foreign nucleic acid is reduced, and, cDNA fragments, for example, may be directionally inserted.

In a significant feature of the present invention, the nucleic acid sequence located between the first and second insertion sites forms an expression blocking sequence (EBS), where as used herein, the term "expression blocking sequence" refers to a nucleic acid sequence which serves to block the expression of downstream nucleic acid, particularly the SEM gene. The EBS is located between the first and second insertion sites forming a removable "EBS cassette".

One preferred embodiment of the EBS acts by blocking the translation of mRNA transcribed from the EBS and associated downstream transcript by ribosomes. Such an EBS is referred to herein as a "translation blocking sequence". A preferred translation blocking sequence includes a sequence which, when transcribed into mRNA, forms a hairpin or other like self-associated structure in the mRNA molecule, e.g., tetra loops, stem loops, pseudo knots, and the like. By forming such a self-associated structure, the efficiency of translation of downstream messenger nucleic acid sequence is greatly reduced.

A second preferred embodiment of the EBS acts by reducing the efficiency of transcription of nucleic acid sequence into mRNA, such a sequence being referred to herein as a "transcription blocking sequence." Rather than disrupting the ribosome-mRNA interaction, the transcription blocking sequence interferes with the RNA-DNA-polymerase interaction. Many such transcription blocking sequences are well known, e.g., stem loops. Preferably, the EBS contains multiple transcription blocking sequences arranged serially.

A third preferred embodiment of the EBS utilizes both a translation blocking sequence and a transcription blocking sequence to block the expression of downstream nucleic acid.

The SEM gene in the cis cloning system is located downstream from the EBS and is physically linked to the EBS such that when the EBS is present, expression of the SEM gene is blocked. Otherwise, the SEM gene performs essentially the same function and has the same properties as the SEM gene described above with reference to the trans cloning system.

The host organism in the cis cloning system serves to provide an environment suitable for maintenance and/or replication of the vector nucleic acid.

Methods employing the cis cloning system utilize cloning techniques well known in the art of molecular biology. First, the vector nucleic acid is cleaved at the first and second insertion sites using an appropriate cleaving agent or combination of cleaving agents under reaction conditions sufficient to render all the cleaving agents active. In the event that the reaction conditions of the two agents are not compatible, two separate reactions may be performed serially. This double cleavage reaction serves to remove the EBS cassette.

The cleaved vector nucleic acid is then contacted with a foreign nucleic acid under conditions sufficient to incorporate the foreign nucleic acid into the vector nucleic acid between the first and second insertion sites, e.g., by enzymatic ligation, thereby forming a recombinant vector nucleic acid. The recombinant vector nucleic acid is then inserted into the host organism by either transfection, transformation, or conjugation, the particular mode of insertion being dependent on the nature of the recombinant vector nucleic acid and the host organism. The host organism is then grown up to provide an opportunity for the expression of the surface-expressed moiety. Finally, the host organism is contacted with a solid support which has been functionalized with a moiety capable of specifically binding to the SEM (see below). If a particular host organism contains a recombinant vector nucleic acid, the host organism will express a SEM at its outer surface and will therefore bind to the functionalized solid support.

3. Tag Insertion Cloning System

In yet a third aspect of the present invention, hereinafter referred to as the "tag insertion cloning system", the recombination of vector nucleic acid and foreign nucleic acid is linked to the expression of a tag moiety (TM) on the surface of the host organism by linking the recombination event with the insertion of a tag moiety sequence into a gene for a protein which is normally expressed on the surface of the host organism. By inserting the TM sequence into the surface-protein gene, the product of the tag moiety sequence is presented to the outside surface of the host organism.

Figure 3:
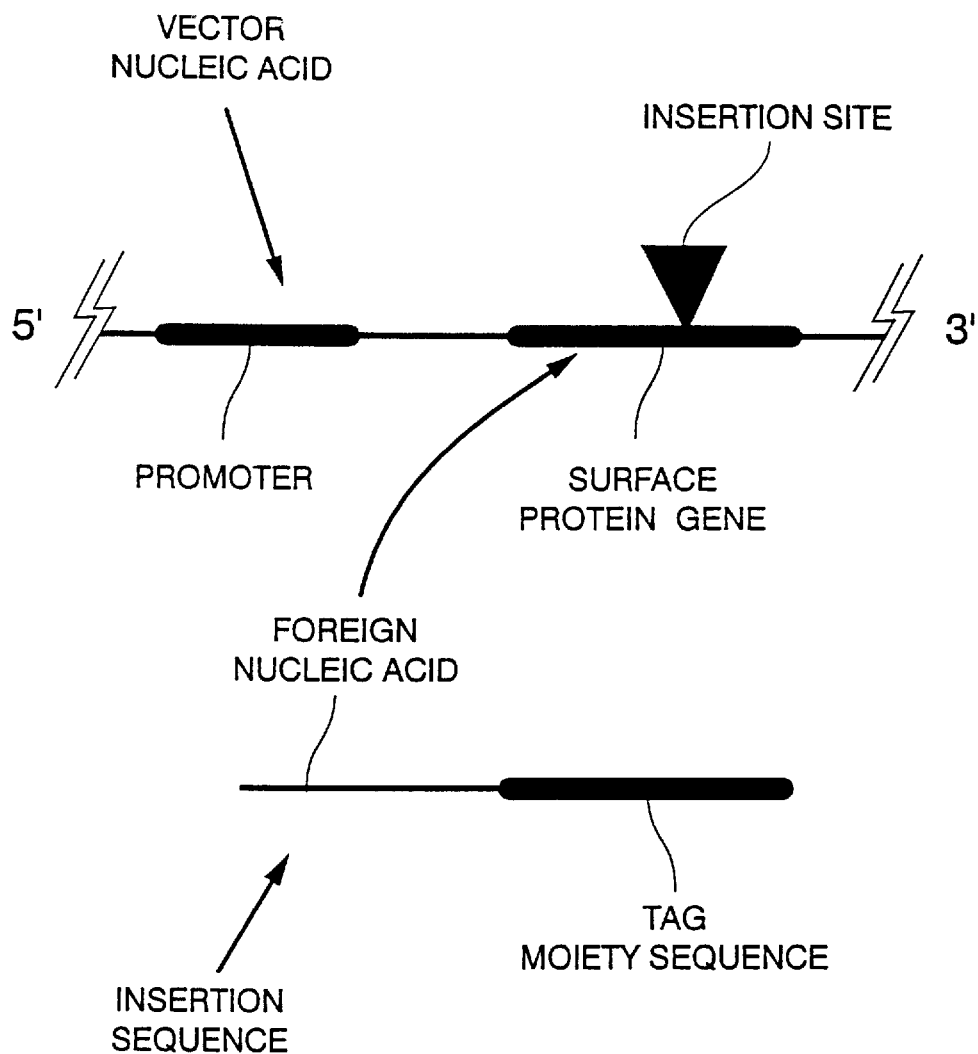
FIG. 3 shows a schematic diagram of the tag cloning system of the present invention.

As shown in FIG. 3, the tag cloning system includes (i) a vector nucleic acid, the vector nucleic acid including (a) a surface-protein gene, (b) an insertion site located within the surface-protein gene, and (c) a promoter functionally linked to the expression of the surface-protein gene; and (ii) an insertion sequence, the insertion sequence including a tag moiety sequence physically linked to a foreign nucleic acid.

The insertion sequence of the present invention is formed by physically linking a foreign nucleic acid sequence with a tag moiety sequence, e.g., by ligation. The foreign nucleic acid and the tag moiety may be linked by any well known ligation means, including chemical ligation or enzymatic ligation.

The surface-protein gene of the present invention codes for a protein that is expressed on the surface of the host organism, i.e., some portion of the surface protein is presented to the environment outside the host organism. Exemplary preferred surface proteins include epidermal growth factor, epidermal growth factor receptor, mating factor, and mating factor receptor. When $E.$ $coli$ is the host organism, preferred surface proteins include maltoporin (Lam B), K88ac and K88ad pilin proteins, TraT lipoprotein, PhoE and OmpA outer membrane proteins, and the OmpA-lipoprotein fusion protein (Lpp-OpmA), e.g., Georgiou et al., Trends Biotechnol., 11: 6–10 (1993).

The tag moiety sequence may be any sequence which codes for a moiety which is a member of a binding pair, e.g., an antigen, an antibody, a receptor ligand and the like, and which can be inserted into the surface-protein gene without disrupting the expression or localization of the surface protein. Alternatively, the tag moiety sequence may be a sequence which, when inserted into the surface protein gene, causes a change in the expression product of the surface protein gene which results in a change in the binding properties of the host organism, e.g., by altering the reading frame of the surface protein gene.

In an important feature of the present invention, the surface-protein gene includes an internal insertion site for inserting the insertion sequence. Preferably, the insertion site is unique within the vector nucleic acid. When the insertion sequence is inserted at the insertion site, the tag-moiety is expressed at the surface of the host organism. Preferably, the insertion site is located in a part of the surface-protein gene which is expected to be located at the outer surface of the host organism when expressed.

Preferably, the vector nucleic acid further includes a promoter sequence functionally linked to the surface-protein gene for promoting the expression of the surface-protein gene.

Methods utilizing the tag cloning system utilize traditional cloning techniques. First, the vector nucleic acid is cleaved at the insertion site using an appropriate sequence-specific cleaving agent, e.g., restriction endonucleases, under conditions sufficient to render the cleaving agent active. Next, the foreign nucleic acid is ligated to the tag moiety sequence, thereby forming an insertion sequence. The cleaved vector nucleic acid is then contacted with the insertion sequence under conditions sufficient to incorporate the insertion sequence into the vector nucleic acid at the insertion site, e.g., by enzymatic or chemical ligation, thereby forming a recombinant vector nucleic acid. The recombinant vector nucleic acid is then inserted into the host organism by either transfection, transformation, or conjugation, the particular mode of insertion being dependent on the nature of the recombinant vector nucleic acid and the host organism. The host organism is then grown up to provide an opportunity for the expression of the surface-protein gene/tag sequence. Finally, the host organism is contacted with a solid support which has been functionalized with a moiety capable of specifically binding to the tag moiety. If a particular host organism contains a recombinant vector nucleic acid, the host organism will express the tag moiety at its outer surface and will therefore specifically bind to the functionalized solid support.

4. Lethal Gene Inactivation System

In a fourth aspect of the present invention, hereinafter referred to as the "lethal gene inactivation system", the recombination of vector nucleic acid and foreign nucleic acid is linked to the insertional inactivation of a lethal gene in the vector. Note that in this system, recombination is indirectly linked to a SEM or tag molecule through the survival of the host organism. Thus, if the recombination event occurs, the host organism survives, the SEM is expressed, and the surviving host organisms can be isolated using a properly functionalized support as described elsewhere.

Figure 4:
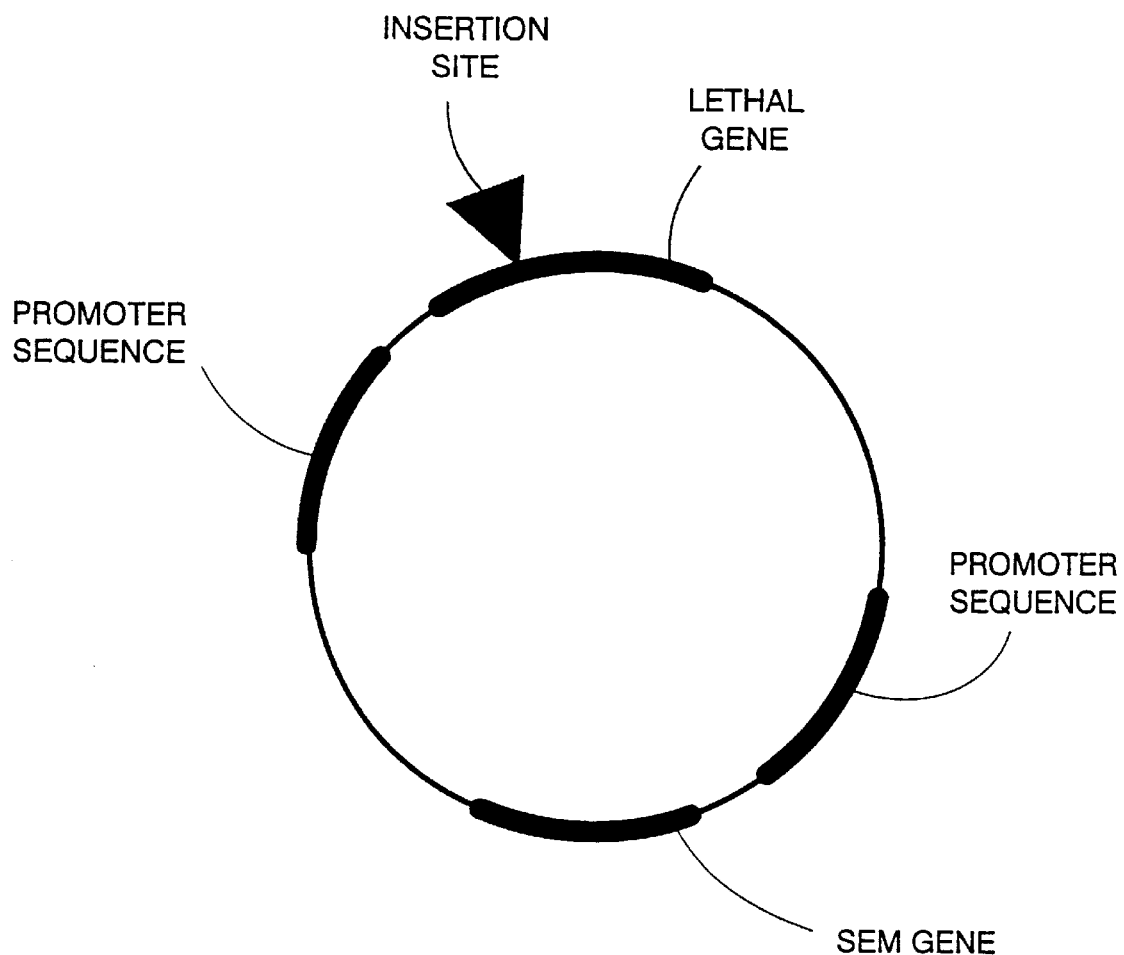
FIG. 4 shows a schematic diagram of the lethal gene inactivation system of the present invention.

As shown in FIG. 4, the lethal gene inactivation system includes a nucleic acid which includes a lethal gene, the expression product of the lethal gene being lethal to a host organism. The nucleic acid of the present system further includes a promoter sequence functionally linked to the lethal gene and an insertion site located within the lethal gene. The insertion site is located such that when foreign nucleic acid is inserted at the insertion site, the lethal gene is insertionally inactivated. Also included in the vector nucleic acid is a surface-expressed-moiety gene, the purpose of which is as described above. In an alternative preferred embodiment, the SEM gene is located on a host nucleic acid.

Preferred lethal genes for $E.$ $coli$ include the active cytotoxic ccdB gene under the control of the lacP promoter, e.g., Bernard et al., Gene, 148: 71–74 (1994).

Methods employing the lethal gene inactivation cloning system utilize cloning techniques well known in the art of molecular biology. First, the nucleic acid of the invention is cleaved at the insertion site using an appropriate cleaving agent or combination of cleaving agents under reaction conditions sufficient to render all the cleaving agents active. The cleaved nucleic acid is then contacted with a foreign nucleic acid under conditions sufficient to incorporate the foreign nucleic acid into the nucleic acid at the insertion site, e.g., by enzymatic ligation, thereby forming a recombinant nucleic acid. The recombinant nucleic acid is then inserted into the host organism by either transfection, transformation, or conjugation, the particular mode of insertion being dependent on the nature of the recombinant vector nucleic acid and the host organism. The host organism is then grown up to provide an opportunity for the expression of the lethal gene and the surface-expressed moiety. Finally, the host organism is contacted with a solid support which has been functionalized with a moiety capable of specifically binding to the SEM (see below). If a particular host organism contains a recombinant nucleic acid, the host organism will survive to express a SEM at its outer surface and will therefore bind to the functionalized solid support.

5. Host Capture System

The host capture system of the present invention provides a means for isolating a host organism which has been transformed with recombinant nucleic acid using any of the cloning systems described above. Generally, the host capture includes a plurality of binding moieties which are attached to a solid support. The binding moieties are members of a binding pair the complementary member of which is differentially expressed on the surface of a host organism, e.g., a SEM, or tag moiety.

Preferably, the binding pair should have an equilibrium dissociation constant ($K_d$) which is in the micromolar or submicromolar range, where, as used herein, the term equilibrium dissociation constant refers to the ratio of unbound to bound binding moieties at equilibrium expressed in concentration units. A dissociation constant in this range facilitates the efficient capture of the recombinant host organisms and provides the requisite selectivity between specifically bound and non-specifically bound host organisms. More preferably, at least one member of the binding pair includes a reactive functional group enabling it to be covalently immobilized to a solid substrate, or to a linker attached to a solid substrate.

Preferably, the binding moiety that is differentially expressed at the surface of the host is chosen such that overexpression of that moiety in the host organism is possible without compromising the viability of the host organism. Such overexpression provides a multiplicity of possible binding sites for binding to the functionalized solid support.

The choice of a particular binding pair is a strong function of the host organism being used. Such binding pairs may be chosen generally among ligand/receptor pairs, antigen/antibody pairs, biotin/avidin pairs, metal/chelator pairs, and any other like binding pairs.

One preferred binding pair useful in cases where *E. coli* is used as the host organism is based on the outer membrane receptor protein FhuA. The FhuA protein binds specifically to a ferrichrome class of siderophores, where as used herein, the term "siderophore" refers to a low-molecular weight iron(III) transport agent produced and utilized by many aerobic microorganisms, e.g., H. Nikaido, Trends Microbiol., 1: 5–7 (1993), and V. Braun, Trends Biochem. Sci., 10: 75–78 (1985). A preferred ferrichrome class siderophore is ferricrocin, e.g., M. Llinas and J. B. Neilands, Bioinorg. Chem., 2: 159–165 (1972).

Additional preferred binding pairs useful in systems using *E. coli* as the host organism include the cell surface determinants flagella/antiflagellin protein, e.g., Macnab, Annu. Rev. Genet., 26: 131–158 (1992) and Silverman et al., Nature, 249: 73–74 (1974); fimbriae/antifimbriae protein or cognate receptors, e.g., Ofek et al., Curr. Top. Microbiol. Immunol., 151: 91–113 (1990), and Gbarah et al., Infect. Immun., 59: 4524–4530 (1991), and Klemm et al., Mol. Microbiol., 4: 553–559 (1990), and Nilsson et al., Bio/Technology, 12: 1376–78 (1994); and lipopolysaccharide (LPS)/anti-LPS protein.

Yet another preferred binding pair system useful in systems using *E. coli* as the host organism is the outer membrane receptor protein BtuB which selectively binds the vitamin B12 class of molecules, e.g., Holroyd et al., in Leive et al. (eds.), Microbiology-1984, p.21–23, American Society for Microbiology, Washington, D.C. (1994).

For gram positive host organisms, preferred binding pairs include the membrane receptor protein FhuD of *Bacillus subtilis* which binds members of the ferrichrome family of siderophores including ferricrocin, e.g., Schneider et al., Mol. Microbiol. 8: 111–121 (1993).

For systems using yeast as a host organism, a preferred binding pair is the membrane α-factor pheromone receptor (Ste2) of the yeast *Saccharomyces cerevisiae* which binds to the mating α factor, e.g., Kurjan, Annu. Rev. Biochem. 61: 1097–1129 (1992).

For systems utilizing mammalian host organisms, preferred binding pairs include the epidermal growth factor/epidermal growth factor receptor pair and the bombesin/bombesin receptor pair, e.g., fantl et al., Annu. Rev. Biochem., 62: 453–481 (1993) and Spindel et al., Recent Prog. Horm. Res. 48: 365–391 (1993).

The solid supports used to immobilize one of the binding moieties are preferably flat, chemically well defined, i.e., chemically homogenous, not water soluble, capable of chemical modification, and wettable by an aqueous solvent. Preferred materials include glass, silicon, plastic, metal, and the like.

In a preferred embodiment of the present invention, the immobilized binding moiety is located at a plurality of discrete anchor sites, where, as used herein, the term "anchor site" refers to a location on the solid substrate having one or more binding moieties attached thereto such that there is an essentially binding-moiety-free region separating each anchor site. Preferably, each anchor site has dimensions such that only a single host organism can bind to a single anchor site. When *E. coli* is the host organism, each anchor site should have an area of approximately 1 square micrometer.

In a more preferred embodiment, the anchor sites are arranged in a high density regular array. By arranging the anchor sites in such a way, the location of each bound host organism can be uniquely determined.

One preferred method of forming an ordered array of covalently immobilized moieties is by using linking groups, where, as used herein, the term "linking group" refers to a chemical species which serves to link a binding moiety to a solid support. Preferred linker molecules have both aqueous and membrane solubility. Particularly preferred linking groups include homopolymers of ω-aminopolyethyleneglycol (PEG) carboxylic acids or ω-aminoalkanoic acids such as ε-aminocaproic acid.

A particularly preferred method of forming a high-density array uses long-chain alkanethiols as linking groups, i.e., molecules having the formula $HS(CH_2)_nX$, where n is preferably greater than 10, and X is an attachment group which facilitates covalent attachment of the binding moiety to the linking group. Long-chain alkanethiols rapidly form ordered, oriented, self-assembled monolayers on evaporated gold films deposited on glass substrates with the attachment group X facing away from the solid support. High resolution patterns of self-assembled monolayers (SAM) of alkanethiolates on gold substrates can be readily fabricated with dimensions as small as 1 μm, e.g., Kumar et al., J. Amer. Chem. Soc. 114:9188–9189 (1992). The dimension of the SAM at each array location or anchor site should not be larger than the projected area of a host organism to ensure that only a single host organism is captured at each location.

Although only a few embodiments have been described in detail above, those having ordinary skill in the molecular biology art will clearly understand that many modifications are possible in the preferred embodiment without departing from the teachings thereof. All such modifications are intended to be encompassed within the following claims.

We claim:

1. A cloning system for expression in a host cell comprising:

a repressor gene coding for a repressor;

a promoter for promoting the expression of the repressor gene;

a restriction endonuclease cleavage insertion site located within the repressor gene or its associated promoter such that when a foreign nucleic acid is inserted at the insertion site, expression of the repressor gene is insertionally inactivated;

a surface-expressed moiety gene; and an operator functionally linked to the expression of the surface-expressed-moiety gene such that when the repressor is bound to the operator expression of the surface-expressed-moiety gene is repressed.

2. The cloning system of claim 1 wherein the first nucleic acid is a host nucleic acid and the second nucleic acid is a vector nucleic acid, wherein the host is cultured cell.

3. The cloning system of claim 1 wherein the first nucleic acid and the second nucleic acid are physically linked.

4. A method for cloning and isolating recombinant nucleic acid comprising the steps of providing a first nucleic acid comprising:

a surface-expressed-moiety gene;

a first promoter sequence for promoting the expression of the surface-expressed-moiety gene; and an operator, said operator being functionally linked to the expression of the surface-expressed-moiety gene such that when a complementary repressor is bound to the operator expression of the surface-expressed-moiety gene is repressed; and a second nucleic acid comprising:

a repressor gene;

a second promoter sequence for promoting the expression of the repressor gene; and an insertion site located within the repressor gene such that when a foreign nucleic acid is inserted at the insertion site expression of the repressor gene is insertionally inactivated;

cleaving the second nucleic acid at the insertion site forming a cleaved second nucleic acid;

contacting the cleaved second nucleic acid with a foreign nucleic acid under conditions sufficient to incorporate the foreign nucleic acid into the cleaved second nucleic acid, thereby forming a recombinant nucleic acid;

inserting the recombinant nucleic acid into a host organism containing the first nucleic acid, wherein the host organism is a cultured cell;

growing the host organism for a time sufficient to express the surface-expressed-moiety gene; and contacting the host organism with a solid support having attached thereto a moiety that specifically binds to the surface-expressed moiety.

5. A cloning system for the isolation of recombinant nucleic acid comprising:

a tag moiety sequence, said sequence being adapted for linking to a foreign nucleic acid thereby forming an insertion sequence; and a nucleic acid comprising:

a surface-protein gene, said gene coding for a protein which is expressed on the surface of a host organism, wherein the host organism is a cultured cell;

a promoter sequence for promoting the expression of the surface-protein gene; and an insertion site located within the surface-protein gene such that when the insertion sequence is inserted at the insertion site the tag moiety sequence is expressed at the surface of the host organism.

6. A method for cloning and isolating recombinant nucleic acid comprising the steps of:

providing a tag moiety sequence, said sequence being adapted for linking to a foreign nucleic acid thereby forming an insertion sequence; and a nucleic acid comprising:

a surface-protein gene, said gene coding for a protein which is expressed on the surface of a host organism, wherein the host organism is a cultured cell;

a promoter sequence for promoting the expression of the surface-protein gene; and an insertion site located within the surface-protein gene such that when the insertion sequence is inserted at the insertion site the tag moiety sequence is expressed at the surface of the host organism;

cleaving the nucleic acid at the insertion site thereby forming a cleaved nucleic acid;

linking the tag moiety sequence with a foreign nucleic acid, thereby forming the insertion sequence;

contacting the cleaved nucleic acid with the insertion sequence under conditions sufficient to incorporate the insertion sequence into the cleaved nucleic acid, thereby forming a recombinant nucleic acid;

inserting the recombinant nucleic acid into a host organism;

growing the host organism for a time sufficient to express the tag moiety sequence; and contacting the host organism with a solid support having attached thereto a moiety that specifically binds to the tag moiety.

7. A cloning system, including a nucleic acid that is expressed in a host organism that is a cultured cell, for the isolation of recombinant nucleic acid comprising:

a surface-expressed-moiety gene;

a first promoter sequence for promoting the expression of the surface-expressed-moiety gene;

a lethal gene, the expression product of the lethal gene being lethal to the host organism;

a second promoter sequence for promoting the expression of the lethal gene; and an insertion site located within the lethal gene such that when foreign nucleic acid is inserted at the insertion site, the lethal gene is insertionally inactivated.

8. A method for cloning and isolating recombinant nucleic acid comprising the steps of providing a nucleic acid comprising:

a surface-expressed-moiety gene;

a first promoter sequence for promoting the expression of the surface-expressed-moiety gene;

a lethal gene, the expression product of the lethal gene being lethal to the host organism;

second promoter sequence for promoting the expression of the lethal gene; and an insertion site located within the lethal gene such that when foreign nucleic acid is inserted at the insertion site, the lethal gene is insertionally inactivated;

cleaving the nucleic acid at the insertion site thereby forming a cleaved nucleic acid contacting the cleaved nucleic acid with a foreign nucleic acid under conditions sufficient to incorporate the foreign nucleic acid into the cleaved nucleic acid, thereby forming a recombinant nucleic acid;

inserting the recombinant nucleic acid into a host organism that is a cultured cell;

growing the host organism for a time sufficient to express the lethal gene and the surface-expressed-moiety gene; and contacting the host organism with a solid support having attached thereto a moiety that specifically binds to the surface-expressed moiety.

9. A method for cloning and isolating recombinant nucleic acid comprising the steps of:

providing a tag moiety sequence, said sequence being adapted for linking to a foreign nucleic acid thereby forming an insertion sequence; and a nucleic acid comprising:
a surface-protein gene, said gene coding for a protein which is expressed on the surface of a host organism, wherein the host organism is cultured cell;
a promoter sequence for promoting the expression of the surface-protein gene; and
an insertion site located within the surface-protein gene such that when the insertion sequence is inserted at the insertion site the tag moiety sequence is expressed at the surface of the host organism;
cleaving the nucleic acid at the insertion site thereby forming a cleaved nucleic acid;
linking the tag moiety sequence with a foreign nucleic acid, thereby forming the insertion sequence;
contacting the cleaved nucleic acid with the insertion sequence under conditions sufficient to incorporate the insertion sequence into the cleaved nucleic acid, thereby forming a recombinant nucleic acid;
inserting the recombinant nucleic acid into a host organism;
growing the host organism for a time sufficient to express the tag moiety sequence; and
contacting the host organism with a solid support having attached thereto a moiety that specifically binds to the tag moiety.

10. A cloning system, including nucleic acid that expresses in a host organism that is a cultured cell, useful for the isolation of recombinant nucleic acid comprising:
a surface-expressed-moiety gene;
a first promoter sequence for promoting the expression of the surface-expressed-moiety gene;
a lethal gene, the expression product of the lethal gene being lethal to the host organism;
a second promoter sequence for promoting the expression of the lethal gene; and
an insertion site located within the lethal gene such that when foreign nucleic acid is inserted at the insertion site, the lethal gene is insertionally inactivated.

* * * * *